United States Patent
Heide

(10) Patent No.: US 11,982,295 B2
(45) Date of Patent: May 14, 2024

(54) PUMPING DEVICE FOR PUMPING LIQUIDS, COMPRISING A CENTRIFUGAL PUMP WITH A RADIALLY PUMPING PUMP WHEEL WITH A HOLLOW CENTER

(71) Applicant: Fresenius Medical Care Deutschland GmbH, Bad Homburg (DE)

(72) Inventor: Alexander Heide, Eppstein (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 791 days.

(21) Appl. No.: 17/254,374

(22) PCT Filed: Aug. 29, 2019

(86) PCT No.: PCT/EP2019/073055
§ 371 (c)(1),
(2) Date: Dec. 21, 2020

(87) PCT Pub. No.: WO2020/043811
PCT Pub. Date: Mar. 5, 2020

(65) Prior Publication Data
US 2021/0268263 A1 Sep. 2, 2021

(30) Foreign Application Priority Data

Aug. 30, 2018 (DE) ........................ 10 2018 006 877

(51) Int. Cl.
*F04D 9/00* (2006.01)
*A61M 60/232* (2021.01)
(Continued)

(52) U.S. Cl.
CPC ........... *F04D 9/004* (2013.01); *A61M 60/232* (2021.01); *A61M 60/538* (2021.01); *F04D 13/06* (2013.01);
(Continued)

(58) Field of Classification Search
CPC ...... F04D 9/004; F04D 13/06; F04D 15/0027; F04D 15/0066; F04D 29/048; F04D 1/00;
(Continued)

(56) References Cited

U.S. PATENT DOCUMENTS 5,873,257 A * 2/1999 Peterson ................ F25B 1/053
62/184
7,798,215 B2 * 9/2010 Leuthen ................ E21B 47/008
166/250.15
(Continued)

FOREIGN PATENT DOCUMENTS

| CN | 105705795 A | 6/2016 |
|---|---|---|
| CN | 108342877 A | 7/2018 |
| DE | 102013017828 | 4/2015 |

OTHER PUBLICATIONS

Centrifugal Pump, Wikipedia, de.wikipedia.org/wiki/Kreiselpumpe.
(Continued)

*Primary Examiner* — Bryan M Lettman
(74) *Attorney, Agent, or Firm* — Jacobson Holman PLLC

(57) ABSTRACT

A pumping device for pumping liquids includes a centrifugal pump with a radially pumping pump wheel having a hollow center, and is configured to remove accumulations of gas from the interior of the pump. The pumping device includes a detecting device for detecting a first operating parameter, a sensor for measuring a second operating parameter, and a control unit for controlling the pump. The control unit is configured to control the operation of the pump so as to remove accumulations of gas from the hollow center of the pump during liquid pumping operation.

13 Claims, 8 Drawing Sheets

(51) Int. Cl.
*A61M 60/538* (2021.01)
*F04D 13/06* (2006.01)
*F04D 15/00* (2006.01)
*F04D 29/048* (2006.01)

(52) U.S. Cl.
CPC ..... *F04D 15/0027* (2013.01); *F04D 15/0066* (2013.01); *F04D 29/048* (2013.01)

(58) Field of Classification Search
CPC ............. F04D 15/0077; F04D 15/0088; F04D 15/0094; A61M 60/232; A61M 60/538
See application file for complete search history.

(56) References Cited

U.S. PATENT DOCUMENTS

| | | | |
|---|---|---|---|
| 7,945,411 B2 * | 5/2011 | Kernan | F04D 15/0088 73/1.16 |
| 2015/0056082 A1 * | 2/2015 | Barrios | F04D 15/0236 417/45 |
| 2016/0084254 A1 * | 3/2016 | Dowling | E21B 43/128 417/44.2 |
| 2016/0222969 A1 | 8/2016 | Heide et al. | |
| 2016/0238263 A1 * | 8/2016 | Meissner | F04D 29/663 |
| 2018/0073509 A1 * | 3/2018 | Madsen | F04D 1/00 |

OTHER PUBLICATIONS

Gülich, Johann.F; Kreiselpumpen Handbuch für Entwicklung; Anlagenplanung und Betrieb; 2013, pp. 294-296, 326-348, 792, 793, 913-915; 4$^{th}$ edition, Springer Vieweg, Germany.

* cited by examiner

Fig. 5 a
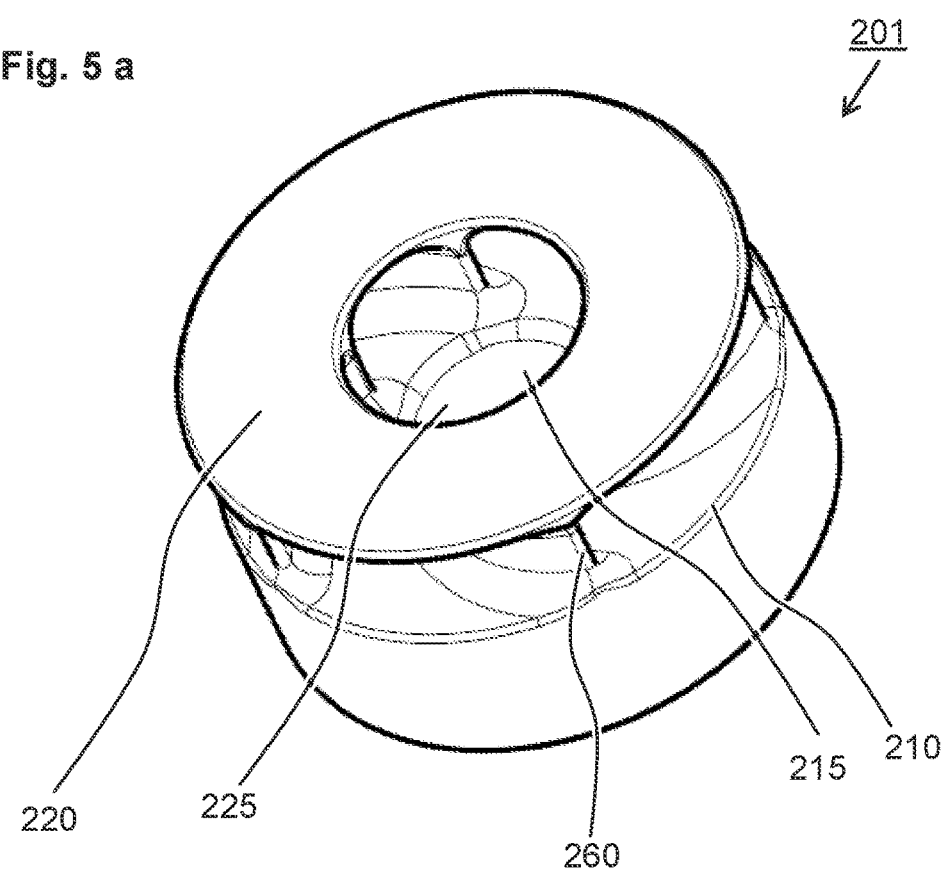
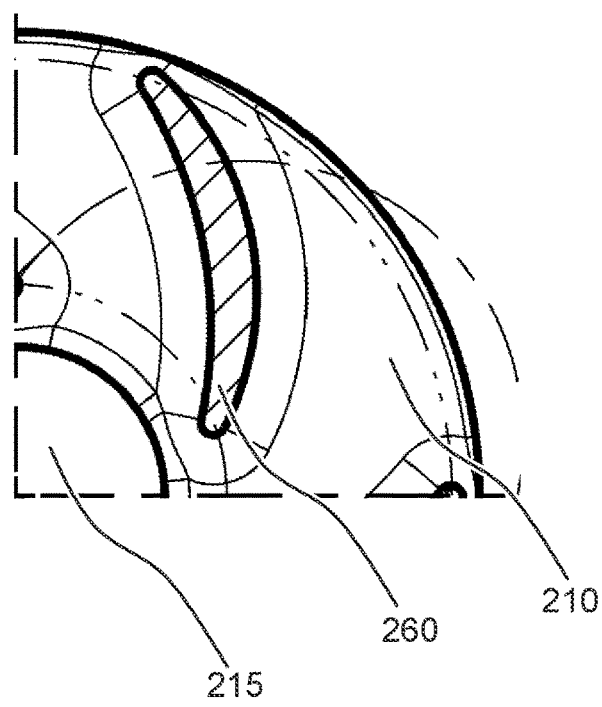
Fig. 5 b

PUMPING DEVICE FOR PUMPING LIQUIDS, COMPRISING A CENTRIFUGAL PUMP WITH A RADIALLY PUMPING PUMP WHEEL WITH A HOLLOW CENTER

BACKGROUND OF THE INVENTION

1. Field of the Invention

The present invention is in the field of pumping devices for pumping liquids, comprising a centrifugal pump with a radially pumping pump wheel with a hollow center.

2. Description of Related Art

Known centrifugal pumps and pumping devices comprising centrifugal pumps comprise rotatable elements in the interior of a pump head, the rotation of which carries a medium to be pumped and, thus, causes it to rotate. The rotational motion results in centripetal forces, which manifest as centrifugal forces in a rotating reference system. When the medium to be pumped enters the interior of a pump essentially centrically at a right angle to the plane of rotation, it is forced outward by the centrifugal forces due to the rotation and thereby transported.

Known centrifugal pumps with a radially pumping pump wheel are used for the transport of gaseous media, for example air for cooling or for fresh air supply, and such pumps are used for transporting liquid media, for example as a fuel feed pump, for pumping process chemicals and for medical applications, among other applications.

Centrifugal pumps are also known as radial-flow rotary pumps. Radial-flow rotary pumps are centrifugal pumps, wherein the medium to be pumped exits the pump wheel radially, The rotor of a pump is occasionally also referred to as a pump wheel.

The present patent application relates to a pumping device for pumping liquids, comprising a centrifugal pump with a radially pumping pump wheel with a hollow center as well as to a centrifugal pump with a radially pumping pump wheel with a hollow center which can be operated at room temperature with liquids and which can transport liquids at room temperature, in particular for use in medical devices, Such pumps can be actively electronically controlled levitating impeller pumps, for example.

Centrifugal pumps with radially pumping pump wheel with a hollow center are radial-flow pumps attributed to the more general category of rotary pumps.

The mass density of liquids transported by liquid pumping centrifugal pumps with a radially pumping pump wheel with a hollow center and pumping devices with a centrifugal pump with a radially pumping pump wheel with a hollow center is typically higher than the mass density of gas mixtures in the liquids thereby pumped, Such gas mixtures may be present originally in the liquids or may be drawn in from the medium surrounding the device by relative vacuums on the intake side of pumping devices—such as air or a process gas, for example. Due to the lower mass density of the gas mixtures and the centrifugal principle of action of the pumps, an accumulation of gas may therefore collect in the interior of the rotating area of the centrifugal pumps during operation of such pumps and pumping devices. The gas admixtures in the liquids may already be undesirable. However, the accumulation of gas in the interior of the pump is definitely unwanted because, for example, the pumping capacity of the pumps can thus be restricted, In the worst case, the pumping capacity may drop due to an accumulation of gas in the interior of a pump to the extent that vacuum generated on the intake side is no longer sufficient to continue pumping the liquid to be pumped.

SUMMARY OF THE INVENTION

One object of the present invention is therefore to make available a device for pumping liquids with a centrifugal pump with a radially pumping pump wheel with a hollow center, which is equipped to remove accumulations of gas from the interior of the pump.

This object is achieved by the pumping device for pumping liquids, comprising a centrifugal pump with a radially pumping pump wheel with a hollow center as described herein, and by the method for removing accumulations of gas from the interior of centrifugal pumps with a radially pumping pump wheel with a hollow center as also described herein. Embodiments and further developments of the idea of the concept according to the invention are the subject matter of dependent claims.

What is disclosed is a pumping device for pumping liquids, comprising a centrifugal pump with a radially pumping pump wheel with a hollow center, a pumping device for conveying blood and/or medical treatment liquids and/or medical treatment waste liquid, a medical treatment device, wherein a pumping device comprising a centrifugal pump with a radially pumping pump wheel with a hollow center is used for pumping blood or a medical treatment liquid or a medical treatment waste liquid, and also relates to a method for removing accumulations of gas from the interior of centrifugal pumps with a radially pumping pump wheel with a hollow center.

The pumping device for pumping liquids comprises at least one centrifugal pump with a radially pumping pump wheel with a hollow center, a detecting device for detecting a first operating parameter, a sensor for measuring a second operating parameter and a control unit for controlling the centrifugal pump, A value of the first operating parameter may be associated with the pump of the pumping device at any point in time during operation, The control unit of the pumping device is connected at least to the pump, to the detecting device for detecting the first operating parameter and to the sensor.

Furthermore, the control unit is equipped to control the operation of the pump. Furthermore, the control unit is equipped so that it can remove accumulations of gas from the hollow center of the pump during liquid transporting operation of the pump. The control unit can remove accumulations of gas by operating the pump in a first step for gas removal so that at least the first operating parameter of the pump varies over time. Varying over time means that the first operating parameter assumes a series of different predetermined values one after the other. While the pump is being operated so that the first operating parameter varies, the associated values of the second operating parameter are in each case recorded in addition to the values of the first operating parameter, i.e., value pairs are stored. These are always pairs of one value of the first operating parameter and of the second operating parameter associated with the first value. In a second step for gas removal, local and/or global extremes of the values of the second operating parameter recorded previously are determined, In a third step for removal of gas, those values of the first operating parameter which are associated with the previously determined extreme values of the second operating parameter are determined. In a fourth step for gas removal, the pump is operated in such a way that, for a predetermined period of time, it assumes at least one of the predetermined values of the first operating parameter which are associated with the extreme values of the second operating parameter.

The method for removing accumulations of gas from the interior of centrifugal pumps with a radially pumping pump wheel with a hollow center is characterized in that it consists of at least the following steps, namely:

operating a centrifugal pump, wherein a first operating parameter of the pump is varied to the extent that the first operating parameter assumes a series of different predetermined values one after the other, meanwhile at least one value of a second operating parameter is recorded for each value of the first operating parameter;

determination of local and/or global extreme values of the previously recorded values of the second operating parameter;

determination of those values of the first operating parameter which are associated with the previously determined extreme values of the second operating parameter;

operating the pump in such a way that, for a predetermined period of time, it assumes one of the values of the first operating parameter associated with the extreme values of the second operating parameter.

The present invention is based on the finding that extreme values of the second operating parameter are obtained when the first operating parameter is adjusted so that the conditions for the conveyance and/or the transport of unwanted accumulations of gas are particularly favorable. Such particularly favorable conditions may include, for example, resonance conditions in the interior of the pump. A pair of one extreme value of the second operating parameter and the associated value of the first operating parameter may thus constitute a resonance condition which is particularly well suited for pumping gas and therefore for removing unwanted accumulations of gas from the pump. To remove unwanted accumulations of gas from the interior of the pump, it is necessary to operate the pump at operating parameters that are particularly suitable for pumping, conveying and/or transporting gas out of the interior of the pump. This is a pumping device for pumping liquids. Such a device is thus primarily equipped to pump liquids. In order to thereby pump/convey/transport gas, for example, to remove unwanted accumulations of gas out of the pumping device itself, special measures must be taken, namely to find and set up certain parameters that have been optimized for this purpose. Normal operation of the device results in an unwanted accumulation of gas in the interior of the pump precisely because the accumulations of gas are not pumped out of the interior of the pump during normal operation of the device.

A centrifugal pump with a radially pumping pump wheel with a hollow center may be an impeller pump. An impeller is thus the pump wheel. The pump wheel is also referred to as rotor of the pump. For example, such a pump wheel may be essentially disk-shaped and may have blades running essentially radially, carrying a pump medium that is to be transported with a rotational motion of the pump wheel. The end of the blades at a distance from the plane of the disk may in turn be connected to another disk arranged to be parallel to the first disk. An embodiment with two disks arranged parallel to one another is just as conceivable as an embodiment with just one disk on which the blades are arranged, whereas the end of the blades remote from the disk is free. A first variant of such a disk has a central recess, i.e., is annular, roughly speaking. An alternative variant of such a disk is embodied as a circular disk thus does not have a central recess.

In the context of the present application, a centrifugal pump with a hollow center is to be understood to mean that the blades extending toward the center do not go as far as the axis of rotation but instead there is a macroscopically discernible region on and/or immediately around the axis of rotation of the pump wheel which is free of blades. However, the hollow center is also not filled with a solid voluminous body, such as a solid cylinder. Instead the center is hollow, so that the liquid to be pumped can flow through the hollow center. It is conceivable for a solid body to lie precisely on the axis of rotation of the pump wheel, for example, an axle or a shaft, In that case, the hollow center is the region situated centrally around the axis of rotation between the solid body and the blades—i.e., the region through which the liquid to be pumped can flow freely.

In the context of the invention, the removal of gas from the device may take place at the time of the initial filling of a liquid system ("priming") or during operation, in particular also during a regular pump operation of a medical treatment device, for example.

A first operating parameter of an existing device may be a pump parameter, i.e., a parameter that can be associated with operation of the pump.

In all embodiments of the present invention, a device for detecting the first operating parameter may be a part of the drive, for example, part of the electrical or electronic power system, of a centrifugal pump. For example, the driving current of the pump may be the first operating parameter. A sensor for detecting a magnetic field may be a device for detecting the first operating parameter. This may be a Hall sensor, for example.

A second operating parameter of the device may be a parameter of state of the device, A proposed apparatus has a sensor for measuring a second operating parameter.

Accumulations of gas in the interior of the pump are unwanted. It is desirable for the entire interior volume of the pump to be filled only with the liquid to be pumped.

A device such as it is proposed in the present patent application is equipped to remove accumulations of gas from the hollow center of the pump. However, that does not mean that accumulations of gas are removed from the interior of the pump continuously during typical operation of such a device. Instead, the accumulations of gas are removed as needed.

Typical values for predetermined periods of time T during which a pump is operated with a certain value of the first operating parameter to remove unwanted accumulations of gas are in the range of 0.01 to 1000 seconds, for example, The periods of time are preferably in the range of 1 to 10 seconds, for example 3 seconds or 5 seconds. In other words, predetermined periods of time T during which a pump is operated to remove unwanted accumulations of gas may be such that the pump assumes the values of the first operating parameter associated with the extreme values of the second operating parameter, for example, in the range of 0.01 to 1000 seconds, preferably in the range of 1 to 10 seconds, for example 3 seconds or 5 seconds.

A sensor for measuring a second operating parameter may also be arranged in or on a liquid line connected to the pumping device or to the pump. An arrangement which can be referred to as being arranged upstream during operation may be considered here in the same way as an arrangement which can be referred to as arranged downstream during operation. It is also conceivable for preferred embodiments of the pumping device proposed here to have more than one sensor for measuring a second operating parameter, for example, one sensor in the immediate vicinity of the pump and a second sensor which is arranged at a distance from the pump on a liquid line connected to it, or a pumping device as proposed here may have a plurality of sensors so that a second operating parameter can be measured both upstream and downstream from the pump. A sensor for measuring a second operating parameter may be, for example, a structure-borne sound sensor.

According to the invention, the extreme values of the second operating parameter mark an operating setting at which accumulations of gas can be transported through the pumping device especially effectively, If resonance occurs in the media located in the transport chamber of the pump during pump operation, then the second operating parameter may assume an extreme value during operation at the resonance condition. In other words, the pairs of values of first operating parameter and second operating parameter, for example, which are characterized by extreme values in the second operating parameter, may be associated with a resonance in the media in the transport chamber of the pump, i.e., also in the hollow center of the pump wheel.

A particularly advantageous embodiment of a pumping device proposed here is set up so that the first operating parameter is a pump rotational speed per unit of time or a pump frequency of the centrifugal pump. This yields the particular advantage that a setting of a direct operating characteristic at which the unwanted accumulations of gas can be transported particularly well, is identified.

In another particularly advantageous embodiment of a pumping device such as that proposed here, the second operating parameter is the noise or structure-borne sound in the liquid to be pumped, measured directly or indirectly on the pumping device. By measuring the noise or structure-borne sound in the liquid, it is possible to identify easily or unambiguously the operating conditions for optimal transport of unwanted accumulations of gas in a particularly advantageous manner.

In another particularly advantageous embodiment of a pumping device such as that device proposed here, the pump is driven electrically, and a first operating parameter is an electrical operating current of the pump or an operating current per rotational speed of the pump. This yields the special advantage that, on the one hand, such an operating parameter can be obtained easily from the usual electrical pump drives without any major technical effort, and, on the other hand, a parameter that correlates directly with pump operation is used.

In another particularly advantageous embodiment of a pumping device proposed here, the pump is an impeller pump mounted to levitate magnetically and a first operating parameter is a bearing current of the pump or a bearing current per rotational speed of the pump. Impeller pumps mounted to levitate magnetically are particularly suitable for certain applications. In particular, a maglev suspension is free of contact and shows practically no wear. By using the bearing current of the pump or the bearing current per rotational speed of the pump as the first operating parameter, this yields the particular advantage that, on the one hand, such an operating parameter can be obtained easily from pump drives for magnetically levitating pumps without any major technical effort and, on the other hand, a parameter that correlates directly with pump operation is used.

In another particularly advantageous embodiment of a pumping device proposed here, the control unit is equipped to remove unwanted accumulations of gas again after carrying out the fourth step, by running through the steps for removing accumulations of gas from the first step to the fourth step again, wherein the recorded values of the first operating parameter of various runs may be different, Since extreme values of the second operating parameter are obtained when the first operating parameter is set so that particularly favorable conditions for the conveyance and/or the transport of unwanted accumulations of gas exist, this embodiment permits a complete removal of unwanted accumulations of gas in a particularly advantageous manner. In the case of partial removal of unwanted accumulations of gas, the result may be a change in the resonance conditions in the interior of the pump. Consequently, there may be a change at which values of the first operating parameter the extreme values of the second operating parameter are present. Thus after unwanted accumulations of gas have been transported out of the pump with a first resonance condition using a first pair of first operating parameter and a second operating parameter, the resonance conditions may be shifted. A renewed determination of the optimal conditions for removing unwanted accumulations of gas can enable a complete, a largely complete or a particularly efficient removal of unwanted accumulations of gas in a particularly advantageous manner. It may also be particularly advantageous to determine new extreme values of the second operating parameter more than twice as a function of the first operating parameter. If a change in the values of the second operating parameter at which maximums occur is detected over various runs, this change may be stored in the form of a protocol file, for example. If maximums persist with no change, then this can be interpreted as a failure with regard to the removal of unwanted accumulations of gas and it can be stored in a protocol file.

In another particularly advantageous embodiment of a pumping device proposed here, the control unit is equipped to carry out the fourth step for several different values of the first operating parameter that are associated with the extreme values of the second operating parameter, It may be a time-saving step in a particularly advantageous manner if a device according to the invention is operated at several values of the first operating parameter in direct succession which are associated with extreme values of the second operating parameter without determining new extreme values in the meantime. Therefore, the time required for the renewed determination of the extreme values can be saved in a particularly advantageous manner, for example, while at the same time gas can be removed from the interior of the pump in a particularly efficient manner because multiple determined values of the first operating parameter are assumed.

In another particularly advantageous embodiment of a pumping device proposed here, the control unit is equipped to vary the first operating parameter in the first step in a linear manner or in jumps with fixed intervals or as interval concatenation which approaches a predetermined value at a predetermined rate. A linear variation provides a simple relationship between the first operating parameter and the second operating parameter in a particularly advantageous manner. A variation at fixed intervals provides a particularly time-saving determination of extreme values as an advantage, A variation with interval concatenation as the approach may be especially advantageous and time-saving and/or may permit particularly accurate knowledge of the extreme values. In another particularly advantageous further development, after varying the first operating parameter in one direction (e.g., a ramp scan from a small value to a larger value), the device is equipped to carry out a variation in the opposite direction in addition or as an alternative. Therefore, measurement errors can be reduced and accuracy can be improved. In advantageous further developments of the devices, the control unit is equipped to carry out a variation with smaller steps (fine scan) after a coarser run through the variation (rough scan). In advantageous further developments, the control unit is equipped to adjust the variation in the first operating parameter as a function of additional parameters of the transported liquid, for example, as a function of its temperature, viscosity, etc.

In another particularly advantageous embodiment of a pumping device proposed here, the control unit is equipped to detect the presence of an unwanted accumulation of gas in the interior of the pump in that the first operating parameter of the pump is monitored continuously or at predetermined intervals during operation of the pump, and its change over time is compared with predetermined detection profiles, and on detection of an accumulation of gas, the removal of accumulations of gas is to be carried out. Therefore it can be made possible in a particularly advantageous manner to output a notification or an alarm with respect to a detected accumulation of gas. In addition, in a further development of the device, it can therefore be made possible in a particularly advantageous manner to provide a device with which the control unit is also equipped to detect accumulations of gas in the interior of the pump and to automatically or after confirmation by a user remove unwanted accumulations of gas from the interior of the pump.

In another particularly advantageous embodiment of a pumping device proposed here, the control unit is equipped to continue the normal liquid transporting operation if no extreme values have been identified in response to the removal of accumulations of gas in the second step. This makes it possible in a particularly advantageous manner to continue normal operation in the absence of an accumulation of gas without any further loss of time. This embodiment is particularly suitable for an operation, in which there is a routine search for extreme values of the second operating parameter.

A particularly advantageous embodiment of a pumping device proposed here is equipped for transporting blood and/or medical treatment liquid and/or medical treatment waste liquid. The proposed apparatus is especially advantageously suitable for use for transporting blood, for example, in extracorporeal blood treatment therapies such as hemodialysis, hemofiltration, hemodiafiltration and apheresis but also in cardiac support therapies. This relates to both the treatment system for chronic therapy as well as systems for acute treatment in intensive care wards. A device proposed here is also particularly advantageous for pumping fresh dialysate, spent dialysate, fresh apheresis liquid and spent apheresis liquid.

BRIEF DESCRIPTION OF THE DRAWINGS

The device and the method are described below with reference to the drawings, in which:

FIG. 5 shows an example of aa pump wheel with a hollowed center for radial pumping, FIG. 8a shows a negative extreme value and FIG. 8b shows a positive extreme value.

The same or similar elements in the figures can be referenced with the same reference numerals.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
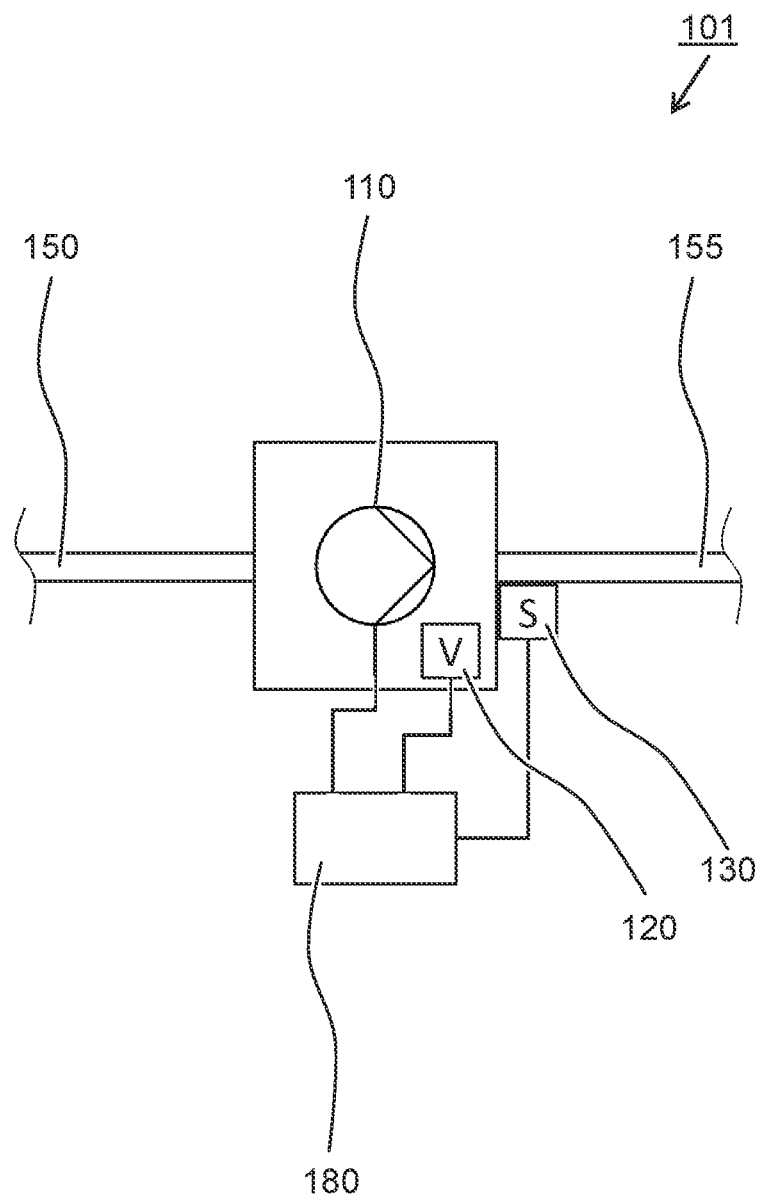
FIG. 1 shows the pumping device according to the invention for pumping liquids, comprising a centrifugal pump with a radially pumping pump wheel with a hollow center, diagrammed schematically in a first embodiment.

FIG. 1 shows schematically a first embodiment of a pumping device 101 according to the invention. The pumping device 101 for pumping liquids has a centrifugal pump 110 with a radially pumping pump wheel with a hollow center. At least one first operating parameter 510 can be allocated to the pump 110 at any time during operation. The figure shows as one option that liquid lines 150, 155 are connected to the pumping device 101: A first line 150 carries the pump medium, i.e., the liquid to be pumped, to the centrifugal pump 110, and a second line 155 removes the liquid to be pumped from the centrifugal pump 110. The first line 150 thus runs upstream, as seen from the pump 110, while the second line 155 runs downstream, as seen from the pump 110. Other options are conceivable for connecting a pumping device proposed here to liquid lines. The connections shown here are to be regarded as one variant, but not as restrictive in any way. The pumping device also has a detecting device 120 for detecting the first operating parameter 510. In the embodiment shown here, the detecting device 120 is mounted on the pump 110 or in its vicinity. One example of such a device has a Hall sensor, for example, which is used with a pump 110, operation of which causes the occurrence of magnetic fields that are variable over time. A Hall sensor located in or on the vicinity of the pump 110 may be used to record the change in magnetic fields and thereby allow inferences about the operating condition of the pump 110. Furthermore, the device 101 has a sensor 130 for measuring a second operating parameter 520 of the device 101. In the variant shown in FIG. 1, the sensor 130 is arranged upstream of the device 101 on the device 101, in the immediate vicinity of the device 101 or near the device 101 or in the second line 155 running downstream. Furthermore, the device has a control unit 180 for controlling the centrifugal pump 110. This control unit 180 of the device 101 is connected to the pump 110, to the detecting device 120 for detecting the first operating parameter 510 of the device 101 and to the sensor 130 for measuring the second operating parameter 520 of the device 101. The control unit 180 controls the operation of the pump 110. It is conceivable for the control unit 180 to control the operation of the entire device 101. The control unit 180 is equipped, so that it can remove accumulations of gas from the hollow center of the pump 110 during operation of the device 101 or during operation of the pump 110. This is to be understood to mean that the interior of the pump 110 is initially mostly filled with the liquid to be pumped but an accumulation of gas develops in the hollow center of the pump during liquid transporting operation of the pump 110 and should now be removed. After successful removal of an accumulation of gas, there is less gas and more liquid in the interior of the pump 110. The control unit 180 is equipped to be able to remove accumulations of gas by operating the pump 110 in a first step for removal of gas and thereby varying the first operating parameter 510 of the pump 110 over time. The first operating parameter 510 may be varied in a ramp form or stepwise, for example. While the pump 110 is being operated and the first operating parameter 510 is being varied, the second operating parameter 520 is also being measured by the sensor 130. This yields values of the second operating parameter 520 as a function of the values of the first operating parameter 510. For example, the pump rotational speed per unit of time is varied as the first operating parameter 510 and structure-borne noise is thereby measured as the second operating parameter. In a second step for removal of accumulations of gas, extreme values E are sought in the previously recorded values of the second operating parameter 520. The values of the first operating parameter 510, which had applied when the extreme values E of the second operating parameter 520 were measured in a third step. In a fourth step for removal of accumulations of gas—in short: for removal of gas—the pump 110 is operated so that, for a predetermined period of time T, it assumes the operating conditions again that existed when the extreme values E of the second operating parameter 520 were measured. These conditions are characterized by the values of the first operating parameter 510 that were determined in the third step. The pump 110 thus assumes the values of the first operating parameter 510 associated with the extreme values of the second operating parameter 520 and does so for a predetermined period of time, e.g., for 5 seconds.

Figure 2:
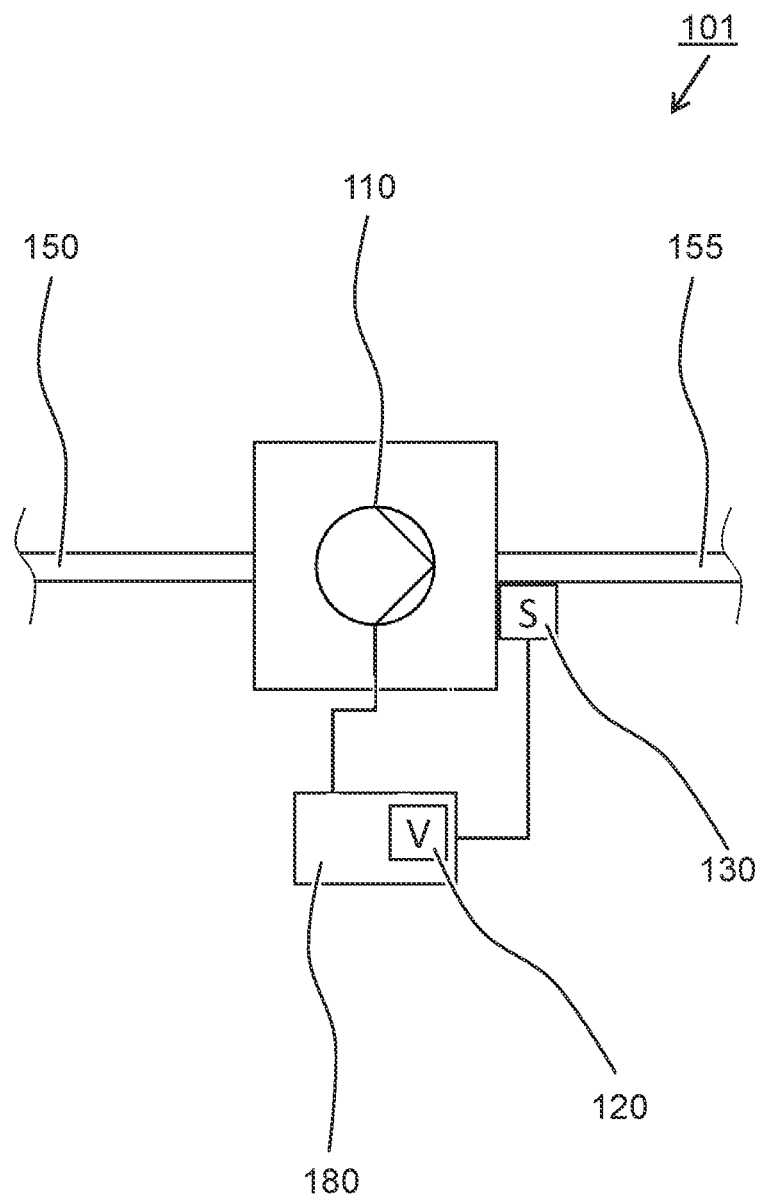
FIG. 2 shows a pumping device according to the invention, in which, in comparison with FIG. 1, the detecting device for detecting the first operating parameter is part of the control unit or is arranged in the control unit.

FIG. 2 shows schematically another embodiment of a pumping device 101 according to the invention. FIG. 2 shows the same elements as FIG. 1, but the detecting device 120 for detecting the first operating parameter 510 is indicated in immediate proximity to the control unit 180 or as an element of the control unit 180. For example, it is conceivable for the first operating parameter to be a parameter of the pump 180, which is detected by the control unit 180 during operation anyway, or which is available to the control unit 180 at least as a signal during operation. This may be the case, for example, when the first operating parameter is a pump current or a bearing current of a pump 110, for example, a magnetically levitating impeller pump 110. It may also be the case if the parameter is a pump frequency or the revolutions of a pump 110 per unit of time, for example, revolutions per minute or per second.

Figure 3:
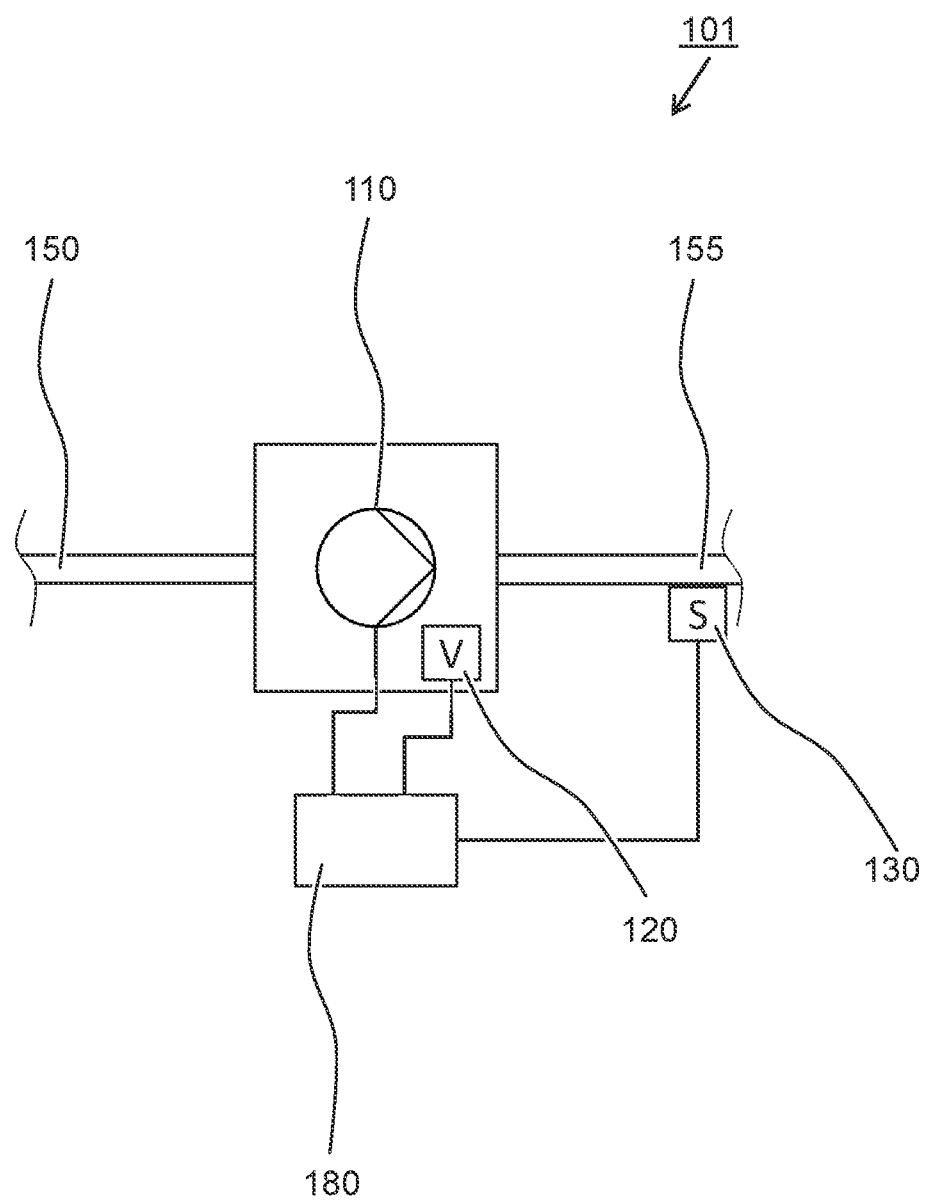
FIG. 3 shows a pumping device according to the invention in which, in comparison with FIG. 1, the sensor for measuring a second operating parameter is arranged in or on a liquid line downstream from the pump and at a distance from the pump, said liquid line being connected to the pumping device and the pump.

FIG. 3 shows schematically another embodiment of a pumping device 101 according to the invention. FIG. 3 shows a pumping device with the same elements as those shown in FIG. 1, but in contrast with the embodiment shown in FIG. 1, the sensor 130 for measuring a second operating parameter 520 here is arranged at a distance from the pump 110 (and an optional pump housing enclosing the pump 110) and is arranged at a distance from the control unit 180 in or on a liquid line leading past the pump. The sensor is thus situated downstream from the pump with respect to the direction of flow of the pumped liquid. The second operating parameter measured here might be, for example, a structure-borne noise and/or sound in the liquid.

Figure 4:
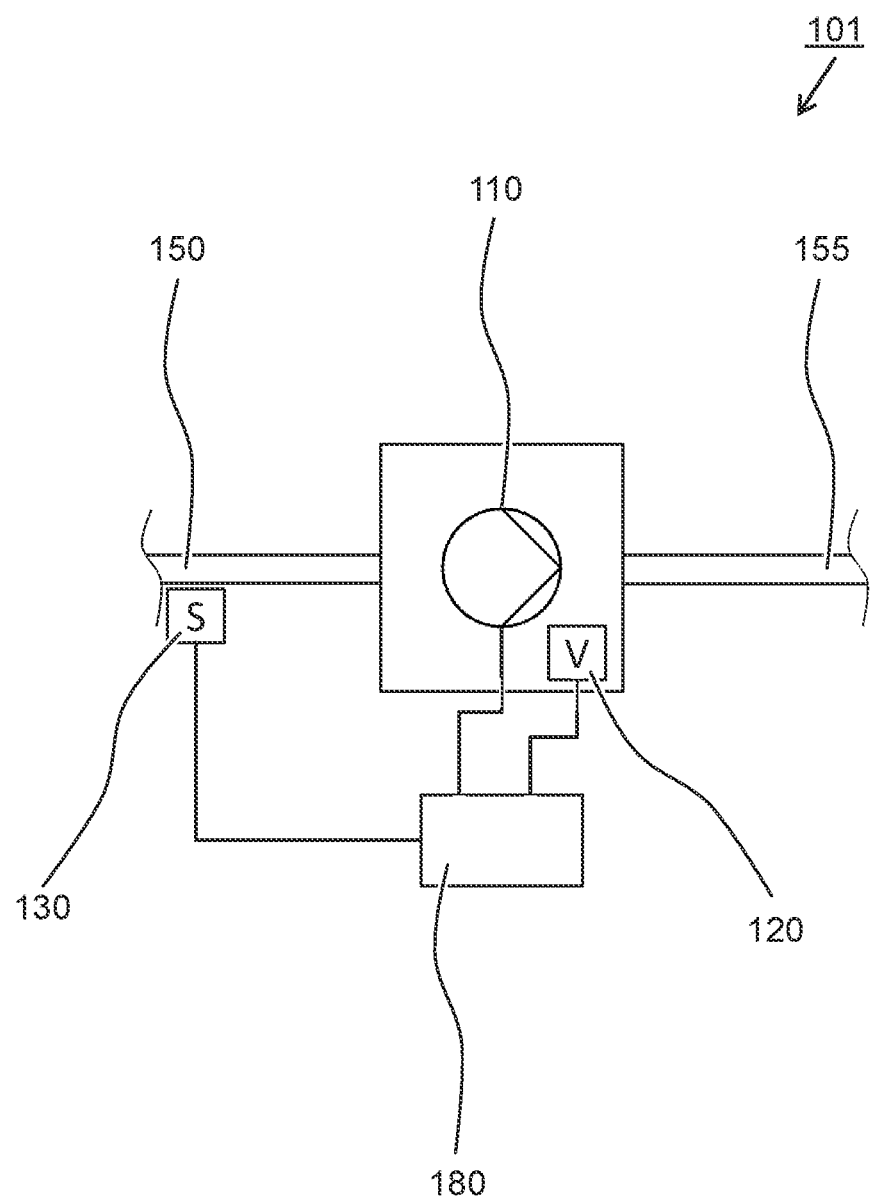
FIG. 4 shows a pumping device according to the invention, in which, in comparison with FIG. 1, the sensor for measuring a second operating parameter is arranged at a distance from the pump, in or on a liquid line upstream from the pump, said line being connected to the pumping device and the pump.

FIG. 4 shows schematically another embodiment of a pumping device 101 according to the invention. FIG. 4 shows a pumping device with the same elements as that shown in FIG. 1, but in contrast with the embodiment shown in FIG. 1, the sensor 130 for measuring a second operating parameter 520 is arranged here at a distance from the pump 110 (and an optional pump housing, enclosing the pump 110) and arranged at a distance from the control unit 180 in or on a liquid line leading to the pump. The sensor is thus situated upstream from the pump with respect to the direction of flow of the liquid being pumped. The second operating parameter measured here might be a structure-borne noise and/or a sound in the liquid, for example.

FIG. 5 shows an example of a pump wheel 201 with a hollow center for radial pumping. A pumping device 101 for pumping liquids with a centrifugal pump 110 with a radially pumping pump wheel 201 with a hollow center might have such a pump wheel 201, for example, FIG. 5 a shows an isometric view of a pump wheel 201, and FIG. 5b shows a partial view of a sectional drawing of the same impeller 201. Basically, the exemplary impeller 201 may be described as two essentially circular disks 210, 220 situated parallel to one another. In one variant, the circular disks 210, 220 may each have a central hole 215, 225, i.e., a hole 215, 225 at and around the midpoint, In an alternative variant, at least one of the circular disks 210, 220 is embodied as a solid circular disk, and the other circular disk 220, 210 has a central hole 225, 215. This diagram attempts to indicate both variants at the same time. In another alternative variant, which is not shown here, the impeller has only one disk 210, 220 and the blades 260 are each free on the end remote from the disk. In another alternative variant (not shown here), the impeller has two disks 210, 220, which do not have a central recess. The two disks 210, 220 are connected to the pump blades 260, which may extend as radial struts between the first disk 210 and the second disk 220. The blades 260 shown here have a radial portion based on the axis of rotation, a tangential portion and a bend, so they are not straight and do not run purely radially or purely tangentially, but instead run "diagonally," so to speak, with a radial and a tangential portion. The hollow center of the pump 110 extends in particular in the region, which is spanned in the illustration shown here by the hole 215 in the first disk 210 and the hole 225 in the second disk 220. However, in all embodiments it is characteristic of the hollow center of the pump 110 that the pump blades 260 (also referred to as blades) do not extend into the hollow center. The hollow center of the pump 110 is thus the region on the axis of rotation of the impeller and/or immediately around it, which is free of pump blades. This region is also not filled by a solid body but instead may flow through free of the liquid to be pumped and in particular also of unwanted accumulations of gas flowing, it is conceivable for a solid body, for example, an axle or a shaft to run directly on the axis of rotation. In this case the hollow center is the region between the axle or the shaft and the pump blades which can be flown through free of the liquid to be pumped.

Figure 6:
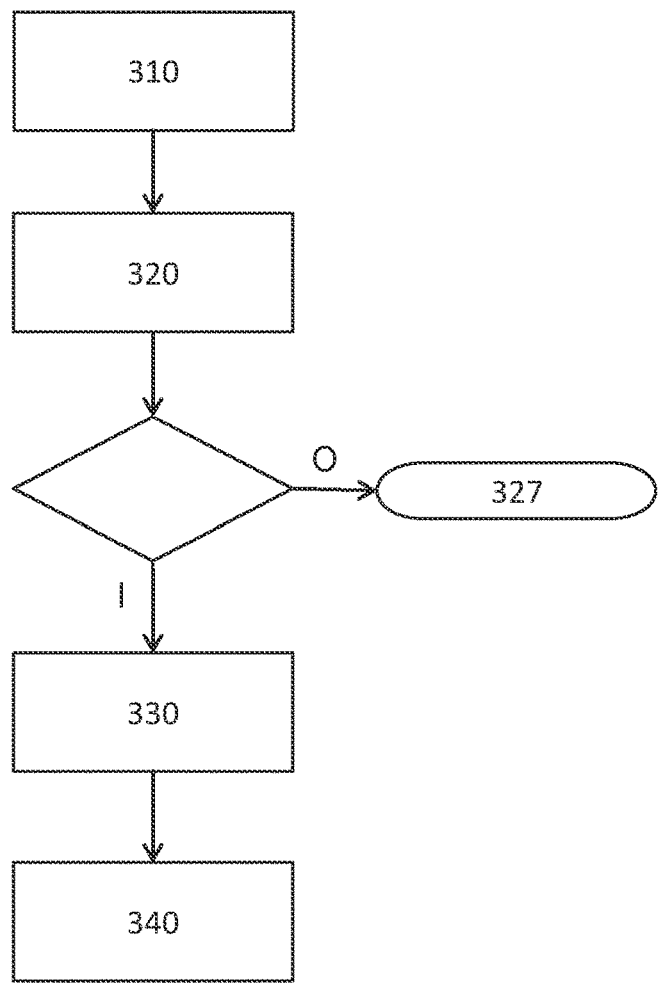
FIG. 6 shows the removal of accumulations of gas according to the invention, schematically in four steps.

FIG. 6 shows a flowchart of a method 301 according to the invention for removing accumulations of gas from the interior of centrifugal pumps 110 with a radially pumping pump wheel 201 with a hollow center. This shows a sequence which can optionally be terminated after determination of extreme values if no extreme values have been detected. This optional review need not occur in all variants of the method. This method has the following method steps:

operating 310 a centrifugal pump, wherein a first operating parameter 510 of the pump 110 is varied to the extent that the first operating parameter 510 assumes a series of different predetermined values one after the other;
during which at least one value of a second operating parameter 520 is recorded for each value of the first operating parameter 510;
determination 320 of local and/or global extreme values E of the previously recorded values of the second operating parameter 520;
optionally: checking on whether extreme values E have been determined; if this check reveals that there is I at least one extreme value E, then the method is continued with the determination 330 of the respective values of the first operating parameter 510. If the check reveals that O there are no extreme values E, then the method is terminated 327;
determination 330 of the values of the first operating parameter 510, which are allocated to the previously determined extreme values E of the second operating parameter 520;
operating 340 the pump in such a way that it assumes one of the values of the first operating parameter 510 allocated to the extreme values E of the second operating parameter 520 for a predetermined period of time.

Figure 7:
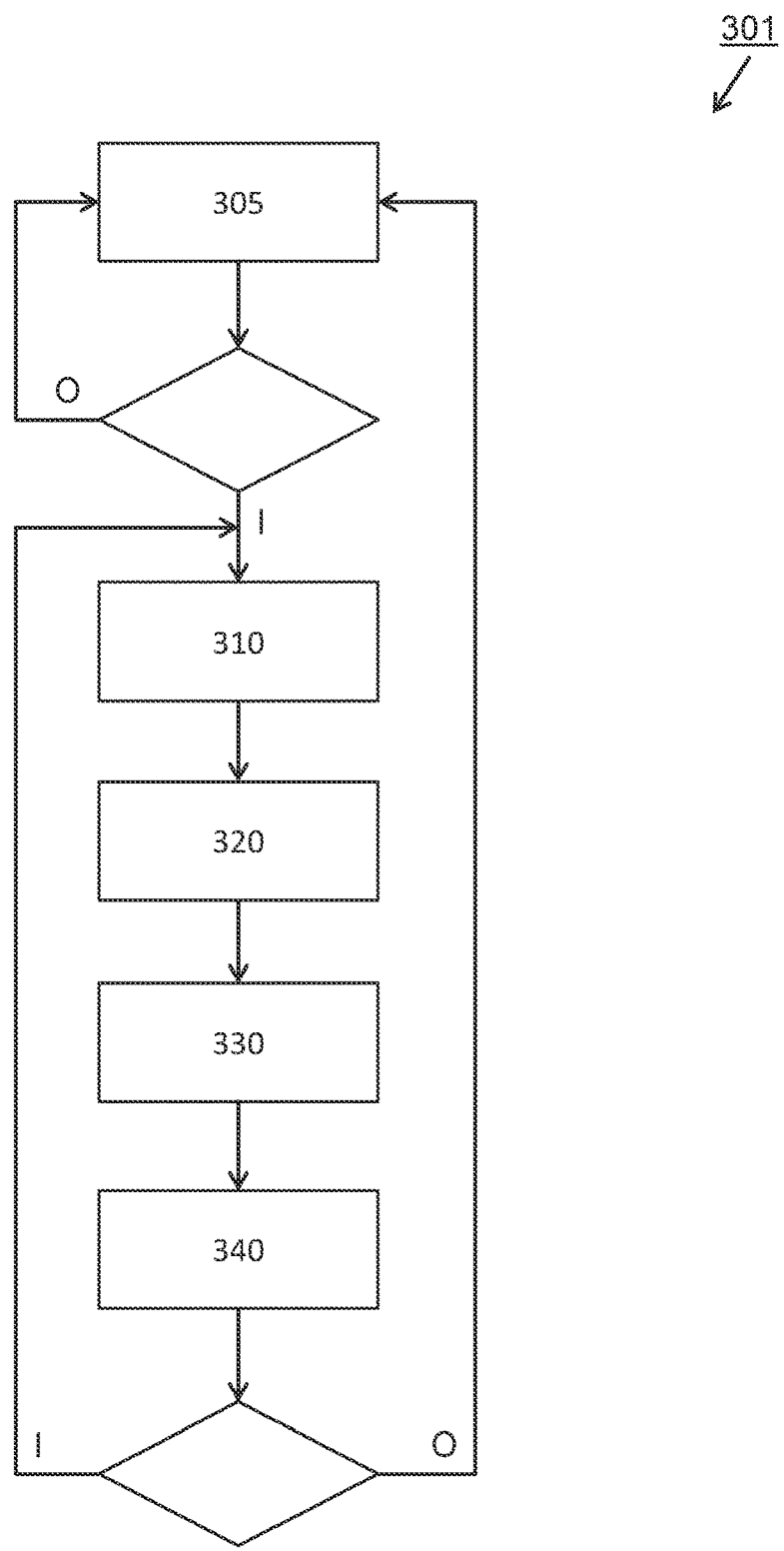
FIG. 7 shows a variant of the removal of accumulations of gas according to the invention, schematically, wherein a detection of accumulations of gas during regular operation and verification of the success of removal are also provided.

FIG. 7 shows another exemplary embodiment of a method 301 according to the invention in the form of a flowchart for removing accumulations of gas from the interior of centrifugal pumps 110 with a radially pumping pump wheel 201 with a hollow center. In contrast with the variant shown in FIG. 6, the pump 110 here is operated continuously, so that an operating parameter of the device 101 is checked 305 continuously or at predetermined intervals during regular operation. The checked parameter may be the first operating parameter 510, for example. On the basis of the values or the change in values of this operating parameter, it is detected when there are accumulations of gas in the interior of the pump 110. To this end, the values of the operating parameter can be compared with predetermined detection profiles, for example. Or exceeding or failing below a predetermined threshold value of the parameter is taken as a sign that there is an accumulation of gas in the interior of the pump 110. Alternatively or additionally, a curve for the development of the parameter, i.e., its trend, may be used to ascertain whether there is an accumulation of gas in the interior of the pump 110. If no accumulation of gas is detected when checking 305 the parameter O, then the regular operation is continued, including continuation of the check 305. If checking 305 on the parameter reveals I that there is an accumulation of gas, then steps are initiated to remove the accumulation of gas as described in conjunction with FIG. 6: varying 310 the first parameter, detecting 320 the first parameter 510 and the second parameter 520, determining 330 the extreme values E of the second parameter 520, determining values 510(E) of the first parameter 510 allocated to the extreme values E of the second parameter 520, operating the pump 110 for a predetermined period of time T wherein the pump 110 assumes a determined value 510(E) of the first parameter 510 allocated to the extreme values E of the second parameter 520. In the variant shown here, after going through these steps, there is optionally also a check on whether an accumulation of gas is still detected in the pump 110. If an accumulation of gas is still detected I in the interior of the pump 110, then the four steps 310, 320, 330, 340 are run through again, whereby the extreme values E need not assume the same values as in the previous run. A change in the extreme values E can be interpreted as a partial success in removal of gas. If an accumulation of gas is no longer detected O, then the regular operation is continued.

Figure 8:
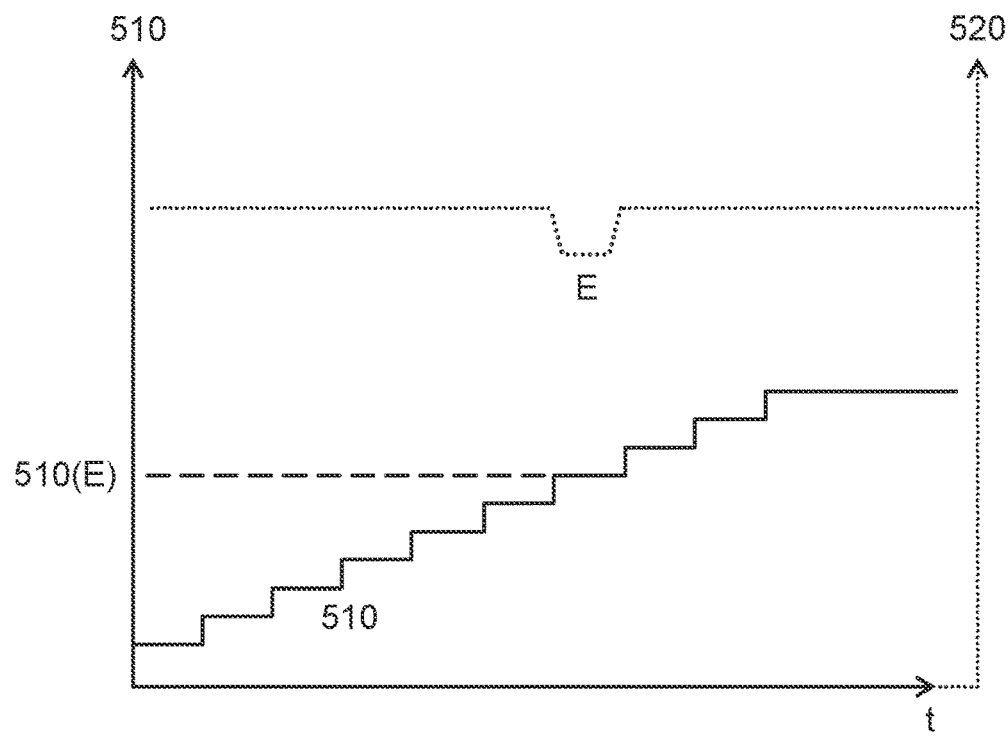
FIG. 8 shows a variation of the first operating parameter according to the invention and simultaneous recording of the second operating parameter as well as an extreme value in the second parameter.
Figure 8:
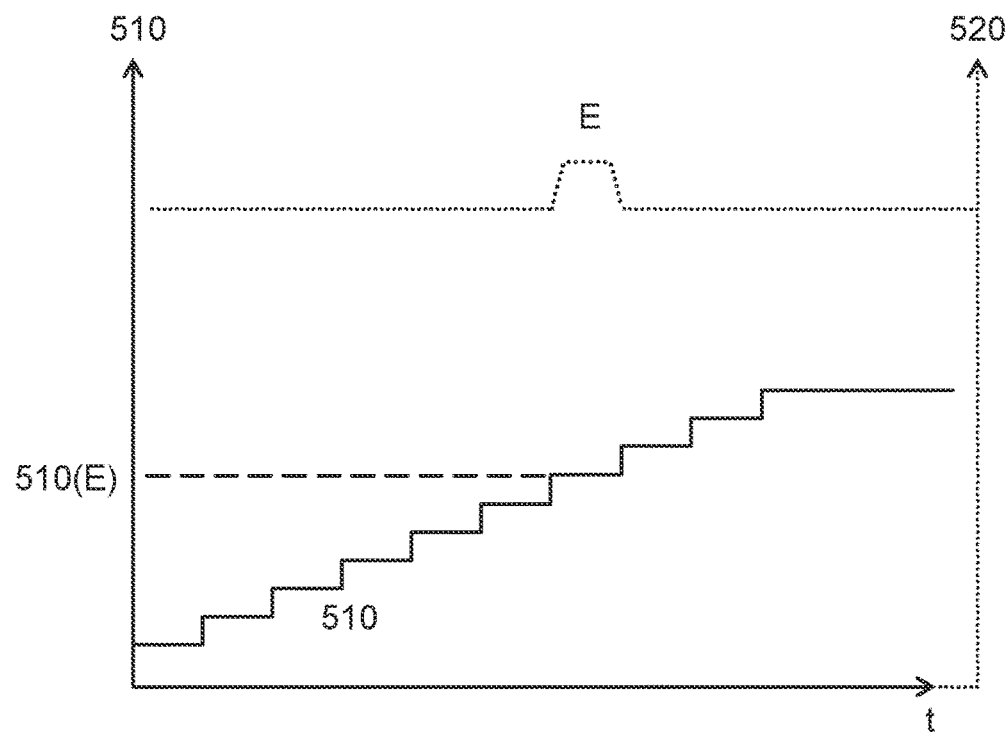

FIG. 8 shows as an example the variation in the first operating parameter 510 over the time t in the form of an idealized step function (shown as a solid line), in which the first operating parameter 510 assumes increasing values over the time t. FIG. 8 a shows as an example an extreme value E of an exemplary second operating parameter 520 which was recorded simultaneously and is a minimum, and FIG. 8b shows an exemplary simultaneous curve of an exemplary second operating parameter 520, which forms an extreme value E in the form of a maximum. In both graphs, the vertical axis on the left corresponds to the size of the value of the first operating parameter 510 in arbitrary units, and the horizontal axis corresponds to the time t. The broken line curve in each case shows the change in the second operating parameter 520, while the first operating parameter 510 is varied as shown here. The right vertical axis with a broken line shows the size of the value of the second operating parameter 520. In both graphs, an extreme value E of the second operating parameter 520 occurs when the first operating parameter 510 assumes a certain value 510(E).

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A pumping device for pumping liquids, comprising
   a. a centrifugal pump with a radially pumping pump wheel having a hollow center, wherein the pump is assigned a value of a first operating parameter at any point in time during operation,
   b. a detecting device for detecting the first operating parameter,
   c. a sensor for measuring a second operating parameter,
   d. and a control unit for controlling the centrifugal pump, which is connected to the centrifugal pump, the detecting device for detecting the first operating parameter and to the sensor, is also equipped so that it controls operation of the pump and removes accumulations of gas from the hollow center of the pump during liquid operation of the pump, by
      operating the pump in a first step for removal of gas so that at least the first operating parameter of the pump is varied over time (t) so that the first operating parameter assumes a series of different predetermined values one after the other,
      and that meanwhile values of the second operating parameter associated with the values of the first operating parameter are recorded,
   determining local and/or global extreme values (E) of the previously recorded values of the second operating parameter in a second step for removal of gas, determining those values of the first operating parameter which are associated with the previously determined extreme values (E) of the second operating parameter in a third step for removal of gas, operating the pump in a fourth step for removal of gas so that it assumes one of the values of the first operating parameter associated with the extreme values (E) of the second operating parameter for a predetermined period of time (T).

2. The pumping device according to claim 1, wherein the first operating parameter is a pump rotational speed per unit of time or a pump frequency of the centrifugal pump.

3. The pumping device according to claim 1, wherein the second operating parameter is structure-borne sound or sound in the liquid to be pumped, measured directly or indirectly on the pumping device.

4. The pumping device according to claim 1, wherein the pump is driven electrically, and the first operating parameter is an electrical operating current of the pump or an operating current per rotational speed of the pump.

5. The pumping device according to claim 4, wherein the pump is an impeller pump mounted to levitate magnetically and a first operating parameter is a bearing current of the pump or a bearing current per rotational speed of the pump.

6. The pumping device according to claim 1, wherein the control unit is equipped to carry out the fourth step for a plurality of different values of the first operating parameter associated with the extreme values (E) of the second operating parameter.

7. The pumping device according to claim 1, wherein the control unit is equipped to remove again any unwanted accumulations of gas after carrying out the fourth step and to do so by running through the steps for removal of the accumulation of gas from the first step to the fourth step again, wherein the recorded values of the first operating parameter of different runs may be different.

8. The pumping device according to claim 1, wherein the control unit is equipped to vary the first operating parameter in the first step in a linear fashion or on jumps at fixed intervals or as interval concatenation, approaching a predetermined value at a predetermined rate.

9. The pumping device according to claim 1, wherein the control unit is equipped to detect the presence of an unwanted accumulation of gas in the interior of the pump by monitoring the first operating parameter of the pump continuously or at predetermined intervals during operation of the pump and comparing any changes in the operating parameter over time with predetermined detection profiles, and carrying out the removal of accumulations of gas if such accumulation of gas is detected.

10. The pumping device according to claim 1, wherein the control unit is equipped to continue a normal liquid pumping operation if no extreme values (E) have been discovered during the removal of accumulations of gas in the second step.

11. The pumping device according to claim 1, wherein the pumping device is configured for transporting blood, medical treatment liquid and/or medical treatment waste liquid.

12. A medical treatment device, comprising the pumping device according to claim 1, wherein the pumping device is used for transporting blood, a medical treatment liquid or a medical treatment waste liquid.

13. A method of removing accumulations of gas from an interior of centrifugal pumps with a radially pumping pump wheel having a hollow center, said method comprising at least the following method steps:

a. operating a centrifugal pump, wherein a first operating parameter of the pump is varied so that the first operating parameter assumes a series of different predetermined values one after the other, i. meanwhile at least one value of a second operating parameter is recorded for each value of the first operating parameter, b. determining local and/or global extreme values (E) of the previously recorded values of the second operating parameter, c. determining those values of the first operating parameter which are associated with the previously determined extreme values (E) of the second operating parameter, d. operating the pump in such a way that it assumes one of the values of the first operating parameter associated with the extreme values (E) of the second operating parameter for a predetermined period of time.

\* \* \* \* \*